United States Patent [19]

Zygraich

[11] 4,341,763

[45] Jul. 27, 1982

[54] METHODS OF VACCINATING HUMANS AGAINST ROTAVIRUS INFECTION

[75] Inventor: Nathan Zygraich, Brussels, Belgium

[73] Assignee: SmithKline-Rit, Belgium

[21] Appl. No.: 242,495

[22] Filed: Mar. 10, 1981

[51] Int. Cl.³ .................. A61K 39/15; A61K 39/225; A61K 39/42

[52] U.S. Cl. .................................. 424/89; 435/236; 435/237; 435/238; 424/86

[58] Field of Search ................................ 424/89, 86

[56] References Cited

U.S. PATENT DOCUMENTS

| | | |
|---|---|---|
| 3,128,230 | 4/1964 | Helmbach . |
| 3,376,198 | 4/1968 | Peterson . |
| 3,838,004 | 9/1974 | Mebus et al. . |
| 3,839,556 | 10/1974 | Mebus et al. . |
| 3,869,547 | 3/1975 | Mebus et al. . |
| 3,873,422 | 3/1975 | Mebus . |
| 3,911,108 | 10/1975 | Singh . |
| 3,919,412 | 11/1975 | Mebus . |
| 3,919,413 | 11/1975 | Mebus . |
| 4,190,645 | 2/1980 | Almeida ................................ 424/89 |

FOREIGN PATENT DOCUMENTS 2616406 10/1977 Fed. Rep. of Germany .

OTHER PUBLICATIONS

Woode et al., *Vet. Rec.* 103:32–34 (1978).
Chanock et al., *JAVMA* 173:570–572 (1978).
Matsuno et al., *Infect. Immun.* 17:661–662 (1977).
In-House Search Report, Mar. 10, 1981.
McNulty et al., *Arch. Virol.* 54:201–209 (1977).
Babiuk et al., *J. Clin. Microbial,* Dec. 1977, pp. 610–617.
Theodoridis et al., *Onderstepoort J. Vet. Res.* 46:65–69 (1979).
Mebus et al., *Can. Vet. J.* 12:69–72 (1971).
Blacklow et al., *New England J. Med.* 304:397–406 (1981).
Bridger et al., "Les Colloques de l'INSERM:", INSERM 90:373–376 (1979).
Yolken et al., Science 201:259 (1978).
Flewett et al., Lancet, Jul. 13, 1974, pp. 61–63.
Kapikian et al., Lancet, May 10, 1975, pp. 1056–1061.
Lancet, Feb. 1975, pp. 257–259.
Zissis et al., *The Lancet,* Jan. 7, 1978, pp. 38–39.
Woode, "Les Colloques de l'INSERM", INSERM 90:15–38.
Wyatt et al., *Science* 203:548–550 (1979).
Bartz et al., *J. Inf. Dis.* 142:439–441 (1980).
Saulsbury et al., *J. Pediat.* 97:61 (1981).
Woode et al., *Res. Vet. Sci.* 16:102–105 (1974).

*Primary Examiner*—Shep K. Rose
*Attorney, Agent, or Firm*—Janice E. Williams; Richard D. Foggio; Alan D. Lourie

[57] ABSTRACT

The invention relates to rotavirus vaccines for man and to methods of using them.

The vaccines comprise an effective dose of bovine rotavirus which is either attenuated or inactivated.

The invention comprises a method of immunizing human beings against human rotavirus infections by administering said vaccines by intramuscular, oral or nasal route; it further comprises a method of immunizing infants by boosting their mother with said vaccines prior to the birth of said infants.

14 Claims, No Drawings

METHODS OF VACCINATING HUMANS AGAINST ROTAVIRUS INFECTION

This invention relates to rotavirus vaccines for man and methods of using them.

In particular the invention comprises live rotavirus vaccines for man obtained for instance by passaging bovine rotavirus in tissue culture until attenuation is obtained and inactivated virus vaccines containing an inactivated bovine rotavirus obtained by inactivation of a virulent or attenuated bovine rotavirus strain.

The invention also comprises a method of immunizing human beings against human rotavirus infections by administering to said human beings a vaccine containing either an attenuated or a killed bovine rotavirus.

The invention further comprises a method of immunizing infants against diarrhoea caused by rotavirus by boosting the mother prior to the birth of said infant with a vaccine containing either an attenuated or, preferably, an inactivated bovine rotavirus, conferring therethrough passive immunization to the infants.

Calf diarrhoea virus vaccines containing either attenuated or killed bovine rotavirus are described in U.S. Pat. Nos. 3,838,004, 3,839,556 and 3,869,547 which are herein incorporated by reference.

The problem of viral diarrhoea is a particularly important topic and recent evidence has indicated that rotaviruses are responsible for the majority of diarrhoeas in infants and young children in both developed and developing countries and may account to a considerable extent for malnutrition owing to associated malabsorption. In infants and young children, the severity of symptoms varies and in the most severe cases, severe dehydration and electrolyte imbalance have been observed. In adults infected with rotavirus, mild diarrhoea or, more commonly, subclinical infection occurs. Treatment of rotavirus disease generally requires standard rehydration therapy. To date no human rotavirus vaccine is known, a reason of such situation being due to the difficult adaptation of human rotavirus to tissue cultures.

Rotavirus has also been shown to be a common intestinal infection in animals and has been demonstrated as a cause of diarrhoea and, more particularly neonatal diarrhoea, in several animal species.

Man, cattle and swine are among the most studied species regarding rotavirus as etiological agents responsible for causing neonatal diarrhoea.

Although rotavirus of different species have a common antigen capable of showing a serological cross reaction (i.e. the fact that an immune serum against the rotavirus originating from a species reacts against rotaviruses originating from the other species), evidence has demonstrated the existence of different serotypes of rotavirus. Indeed, specific immunoserums prepared against the whole purified virus give much higher titers with the homologous virus than with the heterologous viruses.

Recent evidence has demonstrated the existence of several serotypes of human rotavirus and studies of patients who had experienced sequential infections revealed that illness caused by one serotype did not provide protection against illness caused by another serotype (G. ZISSIS et al. The Lancet, Jan. 7, 1978 p. 38-39).

Cross protection studies on animals are very numerous but their results are contradictory. Particularly pertinent references with that regard are given by G. N. WOODE in "Les Colloques de l'INSERM, INSERM," September 1979, 90 p. 15-38 (more particularly p. 27); R. G. WYATT et al. in Science 1979, 203 p. 548-550 and C. R. BARTZ et al. in J. Inf. Dis. 142 No 3 September 1980 p. 439-441.

For instance, according to G. N. WOODE, protection in piglets against the porcine rotavirus cannot be consistently achieved with the bovine rotavirus.

The most likely explanation for this failure is the poor infectivity of the bovine virus for piglets. On the contrary, bovine rotavirus administered in utero to the foetus does protect the calf challenged at birth with human rotavirus, this situation being favourable to the immunizing agent because the virus used originates from the vaccinated animal species.

Surprisingly it has now been found that a bovine rotavirus strain which had previously been passaged 120 times in foetal bovine kidney tissue cultures before being cloned by 3 serial dilutions passages in foetal bovine kidney cultures does protect the 5 to 16 day old colostrum deprived piglet against a challenge of human rotavirus administered on day 28 after birth. The fact that the administered virus does protect the animal against a late infection indicates the induction of an active immune mechanism different from the mechanism which protects calves a few hours after birth and challenged 2-3 days after birth and also from the induction of passive immunity following vaccination of the pregnant cow. The hereinbefore mentioned attenuated bovine rotavirus strain has been deposited on Feb. 25, 1981 with the Collection Nationale de Cultures de Microorganismes (C.N.C.M.) of the Institut Pasteur in Paris where it has been given the collection reference number C.N.C.M. I-148.

The present invention thus related to rotavirus vaccines against human rotavirus capable of inducing immunity in man comprising an effective dose of attenuated bovine rotavirus, preferably stored in freeze-dried form. Effective dosage units are from about $10^4$ to about $10^8$ TCID$_{50}$—and preferably at least $10^{6.5}$ TCID$_{50}$—of virus and the vaccine is administrable by either intramuscular, oral or nasal route after being reconstituted with an adequate diluent, e.g. sterile water. Preferably but not necessarily the vaccine administration is repeated once, e.g. 3 weeks after the first administration. The attenuated bovine rotavirus is for instance the C.N.C.M. I-148 virus.

The invention also relates to a method of immunizing infants and adults human beings against human rotavirus infection by administering them by intramuscular, oral or nasal route a vaccine preparation containing from $10^4$ to $10^8$ TCID$_{50}$—and preferably at least $10^{6.5}$ TCID$_{50}$—of an attenuated bovine rotavirus, said administration being preferably repeated 3 weeks later. The attenuated bovine rotavirus is for instance the C.N.C.M. I-148 virus.

As indicated above the vaccines of the present invention are also possibly administered as inactivated vaccines prepared from either virulent or attenuated bovine rotavirus strain, the virus inactivation being performed according to any technique well known in the art e.g. by treatment with 1/2000 (v/v) formaldehyde.

Although these inactivated vaccines can be administered indistinctly to either adults or infants, they are more particularly intended bor boosting a pre-existing immunity. A particular interesting use of human vaccine containing killed bovine rotavirus is its administration to young women in order to protect their future infant(s) since a recent limited study (F. T. SAULSBURY et al. J. Pediat. 97 No 1 p. 61, 1981) has revealed that for immunodefective patients with chronic rotavirus infection, ingestion of hyperimmune anti rotavirus milk was able to clear rotavirus from the feces and to stop diarrhoea.

Thus, the present invention also relates to inactivated rotavirus vaccines against human rotavirus capable of inducing immunity in man comprising an effective dose of inactivated bovine rotavirus. Preferably the inactivated vaccine is supplemented with an adjuvant for killed vaccine, examples of adequate adjuvant being aluminum hydroxide and calcium phosphate are well known in the art. Effective dosage units are from about $10^4$ to about $10^8$ $TCID_{50}$—and preferably at least $10^{6.5}$ $TCID_{50}$—of virus, said amount being calculated before inactivating the virus. These inactivated vaccines are administrable by either intramuscular or oral or nasal route. Preferably but not necessarily, the vaccine administration is repeated once e.g. 3 weeks after the first administration.

Also included in the present invention is a method of immunizing infants and adults human beings—and preferably boosting the systemic and breast immunity of women of childbearing age—against human rotavirus infection by administering them by intramuscular, oral or nasal route a vaccine preparation containing from $10^4$ to $10^8$ $TCID_{50}$—and preferably $10^{6.5}$ $TCID_{50}$—of an inactivated bovine rotavirus, said amounts being calculated before inactivating the virus, and said administration being preferably repeated 3 weeks later.

It is obvious that the present invention is not restricted to the use of the bovine rotavirus strain C.N.C.M. I-148 which is herein described and used for examplification purpose: the invention applies to the use of any bovine rotavirus isolate and to the attenuated mutants derived thereof, e.g. as disclosed by G. N. WOODE et al. in Res. Vet. Sci. 1974, 16, p. 102–105; M. S. MC NULTY et al. in Arch. Virol. 54, p. 201–209, 1977; L. A. BABIUK et al. in J. Clin. Microbiol. December 1977, p. 610–617 and A. THEODORIDIS ET AL. in Onderstepoort J. Vet. Res. 46, p. 65–69, 1979).

If desired, the attenuated and inactivated vaccines of this invention may be combined to other vaccines, said other vaccines being respectively attenuated or inactivated. Examples of such vaccines are polio vaccines, diphteria-tetanos-pertussis toxoid and colibacillosis bacterial vaccines administrable by the same route as the present rotavirus vaccines.

EXAMPLE 1

Preparation of attenuated rotavirus vaccine

Strain preparation

A typical bovine rotavirus strain (i.e. bovine rotavirus strain Lincoln isolate described by C. A. MEBUS, M. KONO, N. R. UNDERDAHL and M. J. TWIEHAUS in Can. Vet. J. 12, p. 69–72, 1971) passaged 120 times in primary foetal bovine kidney tissue culture was further passaged 4 times in primary foetal bovine kidney tissue culture and then cloned by three serial passages at limiting dilution: 1/24 (positive cupule/inoculated cupules) at a $10^{-7.5}$ dilution, thereafter 1/24 at a $10^{-8}$ dilution and finally 1/24 at a $10^{-7}$ dilution. The supernatant of the positive cupule of the last clone (i.e. passage 127) was coded 'RIT 4237' and underwent two enrichment passages to yield two successive seed batches which were lyophilised in glass vials containing each $10^{6.5}$ $TCID_{50}$ of virus.

The above virus clonings and multiplication steps were all performed in primary foetal bovine kidney tissue cultures. Samples of the second seed batch were deposited at the Collection Nationale de Cultures de Microorganismes, Institut Pasteur, Paris, where they were assigned the collection reference number I.

Vaccine preparation

A sample of the first seed batch is rehydrated and inoculated in primary foetal bovine kidney tissue cultures which are then covered with a maintenance medium consisting of a 50/50 (v/v) mixture of basal and minimal Eagle's media supplemented with 0.25% (w/v) of bovine lactalbumine hydrolysate.

The cells are incubated at 36° C. (±1) until cytopathogenic effect is detected (i.e. from 4 to 7 days after incubation). The culture vessels are then frozen and thawed 3 times, the supernatants are harvested and pooled, peptone (5% v/v) is added thereto and the mixture is distributed into glass vials and lyophilized, the vials are then tightly stoppered, each containing a $10^{6.5}$ $TCID_{50}$ virus titer dosage unit.

For administration, the vaccine is extemporaneously reconstituted with sterile water.

EXAMPLE 2

Potency of attenuated rotavirus vaccine

For activity check the vaccine prepared in Example 1 was tested in an heterologous animal model (piglets) as follows.

In a preliminary step the homologous protection afforded by a human rotavirus of Belgium origin (classified $HRVL_2$) in piglets was evaluated by administering $HRVL_2$ by gastric intubation (IG) to a group of 6 piglets, one week after Caesarian birth. Three weeks later these animals and six control animals were challenged with the same virus. All the controls excreted the challenge virus in their feces whereas none among the previously infected did, demonstrating evidence of complete homologous protection against $HRVL_2$ in piglets.

Dosage units ($10^{6.5}$ $TCID_{50}$) of the vaccine of Example 1 were administered by intramuscular route (IM) to two groups of 6 piglets on day 7 after Caesarian birth and a second dosage unit administered to animals on day 27 after birth, one group being inoculated by the intramuscular (IM) route and the other one being inoculated by gastric intubation (IG). Both groups were thus challenged with $HRVL_2$ excreted by the piglets of the hereabove preliminary trial by gastric intubation (IG) when they were from 34 to 41 days old. A third group of 8 piglets was used as control and received the same challenge of $HRVL_2$ by gastric intubation (IG) when the animals were from 34 to 41 days old. The seroconversion of each animal in the different groups was then checked by different methods (i.e. by seroneutralization (SN), haemagglutination (HI) and Elisa). The results are summarized in Table I from which it appears that (1) two doses of vaccine given 20 days apart stimulate significant serum antibody levels; (2) no difference in antibody response is observed when the vaccine was administered either through two sequential intramuscular inoculations (IM/IM) or one intramuscular inoculation followed by one intragastric inoculation (IM/IG) and (3) after challenge the virus is excreted by almost all control animals and by only a few immunized animals.

The pattern of virus shedding also demonstrated a significant difference between the immunized group and the control group: the ratio of number of virus position specimens detected by the Elisa test on total tested specimens was 8/124 and 25/79 respectively, (p >0.001).

TABLE I

| FIRST INOCULUM | | | |
|---|---|---|---|
| Type | C.N.C.M.I-148 | C.N.C.M.I-148 | None |
| Age (days) | 7 | 7 | — |
| Route | IM | IM | — |
| Seroconversion | | | |
| (SN,HI) | 2/6 | 2/5 | — |
| (Elisa) | 0/4 | 0/6 | — |
| SECOND INOCULUM | | | |
| Type | C.N.C.M.I-148 | C.N.C.M.I-148 | None |
| Age (days) | 27 | 27 | — |
| Route | IM | IG | — |
| Seroconversion | | | |
| (SN,HI) | 6/6 | 5/5 | — |
| (Elisa) | 6/6 | 6/6 | — |
| CHALLENGE | | | |
| Type | Belgian human rotavirus isolate after one passage in piglets | | |
| Age (days) | 24 to 31 | 24 to 31 | 24 to 31 |
| Route | IG | IG | IG |
| Seroconversion | | | |
| (Elisa) (1) | 0/6 | 0/6 | 7/8 |
| Virus shedding (1) | | | |
| (Elisa) | 1/6 | 2/6 | 6/8 |
| (E.M.) (2) | 0/6 | 0/6 | 4/8 |
| Shedding pattern | 8/124 | | 25/79 |

(1) Number of positive animals/Number of tested animals
(2) Electromicroscopy on at least two consecutive days To evaluate the efficacy of the vaccine of Example 1 against human rotaviruses of different origins, the above trial was repeated with one group of 5 piglets receiving two $10^{6.5}$ TCID$_{50}$ dosage units of the vaccine of Example 1 and one group of 5 piglets being kept as control, the challenge virus being a human virus of Bangladesh origin (classified HRVL$_3$). The results are summarized in Table II. Although the challenge virus used in this study was more infectious than the one used in the previous study (shedding pattern 43/95 positive specimens in the control group instead of 25/79 in the previous challenge experiment) the shedding pattern of vaccinated animals was significantly different from the shedding pattern of the control group (p ≦0.001).

TABLE II

| FIRST INOCULUM | | | |
|---|---|---|---|
| Type | C.N.C.M.I-148 | None | |
| Age (days) | 7 to 16 | — | |
| Route | IM | — | |
| SECOND INOCULUM | | | |
| Type | C.N.C.M.I-148 | None | |
| Age (days) | 26 to 35 | — | |
| Route | IG | — | |
| CHALLENGE | | | |
| Type | Human rotavirus from Bangladesh classified as HRVL$_3$ | | |
| Age (days) | 37 to 46 | 7 | 31 to 41 |
| Route | IG | IG | IG |
| Virus shedding (1) | | | |
| (Elisa) | 3/5 | 3/3 | 5/5 |
| Shedding pattern | 9/88 | | 43/95 |

(1) Number of positive animals/Number of tested animals

EXAMPLE 3

Preparation of inactivated rotavirus vaccine

A sample of the C.N.C.M. I-148 strain is rehydrated and inoculated in primary foetal bovine kidney tissue cultures which are then covered with a maintenance medium consisting of basal Eagle's medium supplemented with minimal Eagle's medium containing 0.25% (v/v) of bovine lactalbumine hydrolysate. The cells are incubated at 36° C. (±1) until they show cytopathogenic effect (i.e. from 4 to 7 days after incubation). The supernatants are then harvested, pooled and treated with formaldehyde 1/2000 (v/v).

The inactivated material is distributed in glass vials containing dosage units corresponding to $10^{6.5}$ TCID$_{50}$ before inactivation. The vials are then lyophilised and tightly stoppered to constitute dosage units of inactivated vaccine.

EXAMPLE 4

Potency of inactivated rotavirus vaccine

To evaluate the antigenicity of the inactivated vaccine of Example 1, dosage units of said vaccine were administered to a group of piglets, the vaccination scheme being a first (intramuscular) administration on day 7 after Caesarian birth followed by a second (intramuscular) administration 20 days later. The results are summarized in the following Table III.

Table III shows that the inactivated vaccine administered twice by the intramuscular route is antigenic as evidenced by the stimulation of HI antibodies in 3 out of 4 immunized animals.

TABLE III

| FIRST INOCULUM | |
|---|---|
| Type | Inactivated ($10^{6.5}$ TCID$_{50}$ before inactivation) |
| Route | IM |
| SECOND INOCULUM | |
| Type | Inactivated ($10^{7.5}$ TCID$_{50}$ before inactivation) |
| Route | IM |
| Seroconversion (HI) | |
| 21 days post 2nd dose | 3/4 |

What is claimed is:

1. A method of vaccinating human beings against human rotavirus infection comprising administering by intramuscular, oral or nasal route to said human beings at least one dose of a live vaccine comprising from about $10^4$ to about $10^8$ TCID$_{50}$ of an attenuated bovine rotavirus.

2. The method of claim 1 wherein a second dose is administered by intramuscular, oral or nasal route from 2 to 6 weeks after the first dose.

3. The method of claim 1 wherein the dose is at least $10^{6.5}$ TCID$_{50}$ of attenuated virus.

4. The method of claim 2 wherein each dose is at least $10^{6.5}$ TCID$_{50}$ of attenuated virus.

5. A method of vaccinating human beings against human rotavirus infection comprising administering by intramuscular, oral or nasal route to said human beings at least one dose of an inactivated vaccine comprising from about $10^4$ to about $10^8$ TCID$_{50}$ of bovine rotavirus before inactivation.

6. The method of claim 5 wherein a second dose is administered by intramuscular, oral or nasal route from 2 to 6 weeks after the first dose.

7. The method of claim 5 wherein the dose is at least $10^{6.5}$ TCID$_{50}$.

8. The method of claim 6 wherein each dose is at least $10^{6.5}$ TCID$_{50}$.

9. The method of claim 5 wherein the virus is the C.N.C.M. I-148 virus strain.

10. A method of protecting infants against human rotavirus infection comprising administering to women of child-bearing age by the intramuscular, oral or nasal route at least one dose of an inactivated rotavirus vaccine capable of inducing immunity in man comprising from about $10^4$ to $10^8$ TCID$_{50}$ of bovine rotavirus before inactivation.

11. A method of protecting infants against human rotavirus infection comprising administering to women of child-bearing age by the intramuscular, oral or nasal route at least one dose of an inactivated rotavirus vaccine capable of inducing immunity in man comprising at least $10^{6.5}$ TCID$_{50}$ of bovine rotavirus before inactivation.

12. The method of claim 10 wherein a second dose is administered by intramuscular, oral or nasal route from 2 to 6 weeks after the first dose.

13. The method of claim 11 wherein a second dose is administered by intramuscular, oral or nasal route from 2 to 6 weeks after the first dose.

14. The method of claim 10 or 11 wherein the virus is the C.N.C.M. I-148 virus strain.

* * * * *